US00PP16336P2

(12) United States Plant Patent
Nouws

(10) Patent No.: US PP16,336 P2
(45) Date of Patent: Mar. 14, 2006

(54) ***SORBARIA* PLANT NAMED 'SEM'**

(50) Latin Name: *Sorbaria sorbifolia*
Varietal Denomination: Sem

(75) Inventor: Joannis Jacobus Petrus Nouws, Zundert (NL)

(73) Assignee: Witteman & Company, Hillegom (NL)

( * ) Notice: Subject to any disclaimer, the term of this patent is extended or adjusted under 35 U.S.C. 154(b) by 86 days.

(21) Appl. No.: 10/878,421

(22) Filed: Jun. 28, 2004

(51) Int. Cl.
*A01H 5/00* (2006.01)

(52) U.S. Cl. ..... Plt./226

(58) Field of Classification Search ..... Plt./226, Plt./373

See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Sorbaria* plant named 'Sem', characterized by its compact, upright and outwardly spreading plant habit; bronze-colored developing foliage; and green-colored fully expanded foliage.

2 Drawing Sheets

Botanical classification/cultivar designation: *Sorbaria sorbifolia* cultivar Sem.

BACKGROUND OF THE INVENTION

The present Invention relates to a new and distinct cultivar of *Sorbaria* plant, botanically known as *Sorbaria sorbifolia,* and hereinafter referred to by the cultivar name 'Sem'.

The new *Sorbaria* originated from a cross-pollination of two unnamed selections of *Sorbaria sorbifolia,* not patented, by the Inventor during the summer of 1998. The *Sorbaria* was discovered and selected as a single plant by the Inventor in a controlled environment in Zundert, The Netherlands, during the summer of 2000 from the resultant progeny of the cross-pollination.

Asexual reproduction of the new cultivar by cuttings taken at Zundert, The Netherlands, since 2000 has shown that the unique features of this new *Sorbaria* are stable and reproduced true to type in successive generations.

SUMMARY OF THE INVENTION

Plants of the cultivar Sem have not been observed under all possible environmental conditions. The phenotype may vary somewhat with variations in environment such as temperature and light intensity without, however, any variance in genotype.

The following traits have been repeatedly observed and are determined to be the unique characteristics of 'Sem'. These characteristics in combination distinguish 'Sem' as a new and distinct cultivar of *Sorbaria:*

1. Compact, upright and outwardly spreading plant habit.
2. Bronze-colored developing foliage.
3. Green-colored fully expanded foliage.

Plants of the new *Sorbaria* are most similar to and can be compared to plants of the unnamed parent *Sorbaria* selections. In side-by-side comparisons conducted in Zundert, The Netherlands, plants of the new *Sorbaria* differed from plants of the parent selections in the following characteristics:

1. Plants of the new *Sorbaria* were more compact and shorter than plants of the parent selections.
2. Plants of the new *Sorbaria* had bronze-colored developing foliage whereas plants of the parent selections had green-colored developing foliage.
3. Plants of the new *Sorbaria* had lighter green-colored fully expanded foliage than plants of the parent selections.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Sorbaria.*

The photograph on the first sheet comprises a side perspective view of a typical plant of 'Sem' grown in a container.

The photograph at the top of the second sheet is a close-up view of typical developing foliage of 'Sem'.

The photograph at the bottom of the second sheet is a close-up view of typical fully expanded foliage of 'Sem'.

DETAILED BOTANICAL DESCRIPTION

Plants shown in the aforementioned photographs and used in the following description were grown in 3-liter containers and under conditions which closely approximate commercial production conditions during the summer in an outdoor nursery in Zundert, The Netherlands. Plants were about two years old when the photographs and description were taken. During the production of the plants, day temperatures ranged from 14 to 30° C. and night temperatures ranged from 7 to 14° C. In the following description, color references are made to The Royal Horticultural Society Colour Chart, 2001 Edition, except where general terms of ordinary dictionary significance are used.

Botanical classification: *Sorbaria sorbifolia* cultivar Sem.

Parentage:

*Female, or seed, parent.*—Unnamed selection of *Sorbaria sorbifolia,* not patented.

*Male, or pollen, parent.*—Unnamed selection of *Sorbaria sorbifolia,* not patented.

Propagation:

*Type.*—By cuttings.

*Time to initiate roots.*—About 15 days at 18° C.

*Time to produce a rooted young plant.*—About six months at 12° C.

*Root description.*—Fine, fibrous; brownish white in color.

*Rooting habit.*—Dense, freely branching.

Plant description:

*Form.*—Deciduous shrub; perennial. Compact, upright and outwardly spreading plant habit; broad inverted triangle. Moderately vigorous growth habit.

*Growth rate.*—About 15 months are required to produce fully-grown plants.

*Plant height.*—About 30 cm.

*Plant width.*—About 37 cm.

*Lateral branch description.*—Number per plant: About seven. Length: About 19.4 cm. Diameter: About 3.5 mm. Internode length: About 2.4 cm. Texture: Smooth, glabrous. Strength: Strong. Color: 144A.

*Foliage description.*—Arrangement: Alternate; compound, odd-pinnate; about 13 leaflets per leaf; leaflets sessile. Leaf length: About 17.2 cm. Leaf width: About 11.1 cm. Leaflet length: About 5.2 cm. Leaflet width: About 1.7 cm. Leaflet shape: Lanceolate. Leaflet apex: Apiculate, elongated. Leaflet base: Attenuate. Leaflet margin: Biserrate. Leaflet texture, upper and lower surfaces: Smooth, glabrous. Leaflet venation pattern: Pinnate. Leaflet color: Developing foliage, upper surface: 164B slightly overlain with 144B. Developing foliage, lower surface: 161A slightly overlain with 144B to 144C. Fully expanded foliage, upper surface: 137A. Fully expanded foliage, lower surface: 138A. Venation, upper surface: 144A. Venation, lower surface: 144A to 144B. Petiole length: About 4.2 cm. Petiole diameter: About 2 mm. Petiole texture, upper and lower surfaces: Smooth, glabrous. Petiole color, upper surface: 178A to 178B. Petiole color, lower surface: 144A.

Flower description: Flower development has not been observed on plants of the new *Sorbaria.*

Disease/pest resistance: Plants of the new *Sorbaria* have not been noted to be resistant to pathogens and pests common to *Sorbaria.*

Temperature tolerance: Plants of the new *Sorbaria* have been observed to tolerate temperatures from −20 to 35° C.

It is claimed:

1. A new and distinct cultivar of *Sorbaria* plant named 'Sem', as illustrated and described.

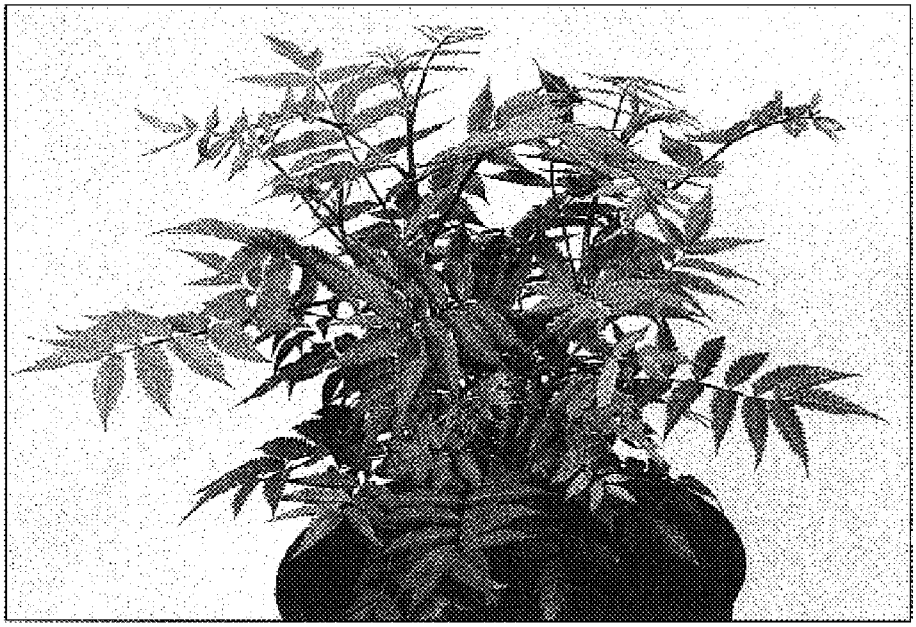

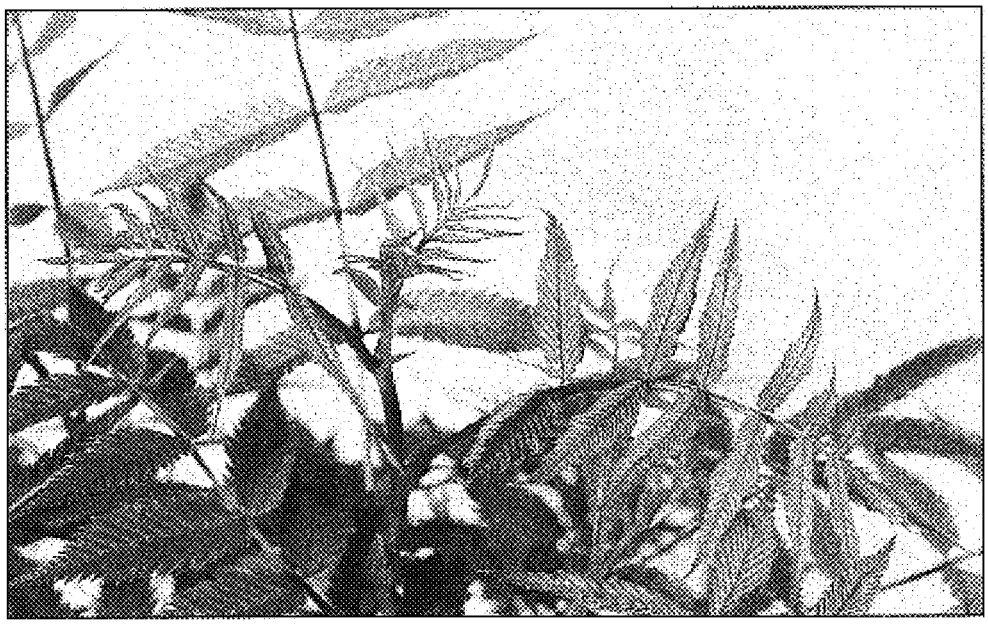
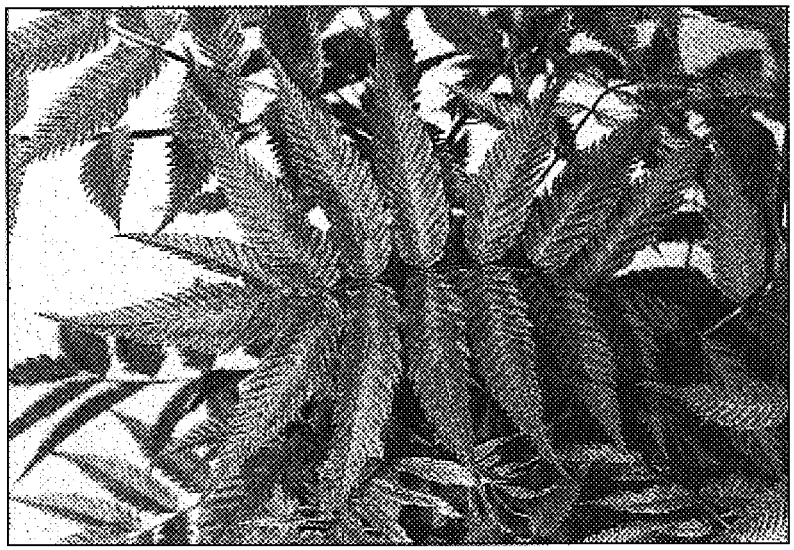

* * * * *